(12) United States Patent
Millar et al.

(10) Patent No.: US 7,182,847 B1
(45) Date of Patent: Feb. 27, 2007

(54) SYSTEM AND PROBE FOR MONITORING PH LEVELS OF A SAMPLE MEDIUM

(75) Inventors: Huntly D. Millar, Houston, TX (US); Robert L. Pauly, Friendswood, TX (US)

(73) Assignee: Millar Instruments, Houston, TX (US)

( * ) Notice: Subject to any disclaimer, the term of this patent is extended or adjusted under 35 U.S.C. 154(b) by 687 days.

(21) Appl. No.: 10/431,132

(22) Filed: May 7, 2003

(51) Int. Cl.
 *G01N 27/333* (2006.01)
(52) U.S. Cl. .................. 204/433; 204/435; 205/787.5
(58) Field of Classification Search .............. 204/433, 204/435; 205/787.5
 See application file for complete search history.

(56) References Cited

U.S. PATENT DOCUMENTS

| | | | |
|---|---|---|---|
| 3,742,594 A | | 7/1973 | Kleinberg |
| 3,855,095 A | * | 12/1974 | Leonard et al. ............. 204/420 |
| 4,162,211 A | * | 7/1979 | Jerrold-Jones .............. 204/420 |
| 4,561,963 A | | 12/1985 | Owen et al. |
| 4,681,116 A | | 7/1987 | Settler |
| 4,927,518 A | * | 5/1990 | Tauber et al. ................ 204/421 |
| 5,158,083 A | * | 10/1992 | Sacristan et al. ........... 600/361 |
| 5,470,453 A | * | 11/1995 | Nipkow et al. ............. 204/435 |
| 5,603,817 A | | 2/1997 | Settler et al. |
| 5,690,680 A | | 11/1997 | Settler et al. |
| 5,766,432 A | | 6/1998 | Dunn et al. |
| 6,495,012 B1 | * | 12/2002 | Fletcher et al. ............. 204/435 |
| 2003/0150726 A1 | * | 8/2003 | West et al. .................. 204/433 |

OTHER PUBLICATIONS

Orion 1997 Laboratory Products and Electrochemistry Handbook, pp. 4-14 and 86.*
Syringe Needle Conversion Chart from Sigma-Aldrich 2006.*
Rosenfeldt et al., "Evaluation of a miniature antimony electrode for measurement of myocardial pH," Journal of Medical Engineering & Technology, vol. 23, No. 4, 1999, pp. 119-126.
Ota et al., "Antimony electrode for the determination of the intramyocardial pH during open-heart surgery," Clin. Phys. Physiol. Meas., vol. 13, No. 4, 1992, pp. 335-347.
Dhalla et al., "The Suitability of the Antimony Electrode for pH Determination in Mammalian Heart," Journal of Pharmacological Methods, vol. 3, 1980, pp. 221-234.
Yates et al., "Modification of intramuscular pH oscillations in the isolated perfused rat heart by different interventions," © 1979 National Research Council of Canada, pp. 900-907.

* cited by examiner

*Primary Examiner*—Kaj K. Olsen
(74) *Attorney, Agent, or Firm*—Charles D. Huston; Daffer McDaniel, LLP (57) ABSTRACT

A system for monitoring a pH level of a sample medium is disclosed herein as including a pH probe having a pH-sensitive electrode, a reference electrode and a temperature electrode arranged within a housing of the pH probe. The probe housing generally includes a flexible inner tube and a flexible outer tube, the inner tube being concentrically arranged within the outer tube. Preferably, a size of the probe housing minimizes the amount of trauma introduced by insertion of the pH probe into physiological tissues, muscles or fluids. The system also includes a processing means, which is coupled to the pH probe for determining the pH of the sample medium. A method of forming a pH-sensitive electrode, a method of manufacturing a pH probe, and a method for using a pH probe are also disclosed herein.

17 Claims, 5 Drawing Sheets

SYSTEM AND PROBE FOR MONITORING PH LEVELS OF A SAMPLE MEDIUM

BACKGROUND OF THE INVENTION

1. Field of the Invention

This invention relates to a system, method and probe for use in measuring hydrogen ion concentrations, or pH, in a sample medium and, more particularly, to a minimally invasive, micro-sized pH probe having a pH-sensitive electrode, a reference electrode and a temperature electrode arranged within a probe housing. Preferably, a size of the probe housing minimizes the amount of trauma introduced by insertion of the pH probe into physiological tissues, muscles, or fluids.

2. Description of the Related Art

The following descriptions and examples are not admitted to be prior art by virtue of their inclusion within this section.

Generally speaking, pH is a measure of the hydrogen ion ($H^+$) concentration within an aqueous solution. More specifically, pH is an indication of the acidity or alkalinity of a solution, and is defined as the negative logarithm of the $H^+$ concentration. A solution having a pH value of 7.0 is typically considered a neutral solution, whereas lower pH values (i.e., higher $H^+$ concentrations) indicate acidic solutions and higher pH values (i.e., lower $H^+$ concentrations) indicate basic or alkaline solutions. In this manner, the acidity or alkalinity of a solution may be measured on a pH scale of about −2 to about 16. For each pH unit above 7.0, the $H^+$ concentration is decreased tenfold, and vice versa.

In physiological solutions, maintenance of proper pH levels is critical, due to the pH dependency of chemical reactions that occur in the body. For example, all cells in the body continually exchange chemicals (e.g., nutrients, waste products, and ions) with interstitial fluids, which in turn, exchange chemicals with plasma in the bloodstream. A dominant mode of exchange between these fluids (i.e., intracellular fluid, interstitial fluid, and blood plasma) is diffusion through membrane channels, due to a concentration gradient associated with the chemical composition (and thus the pH) of these fluids. In order to maintain proper pH levels inside the cells, pH levels outside the cells must be kept relatively constant. This constancy is known in biology as $H^+$ homeostasis.

Cellular health begins to decline when $H^+$ homeostasis between the intracellular fluid, interstitial fluid and blood plasma is not maintained. As an example, the normal pH of (arterial) blood plasma, otherwise referred to as "physiological pH," is about 7.4. If, for instance, pH levels of the blood plasma and interstitial fluid are too low (i.e., less than about 7.35), an excess of hydrogen ions will enter the cell, thereby increasing the acidity of the intracellular fluid and creating a condition called "acidosis." Examples of conditions that cause physiological pH to drop may include hypoxia due to, for example, hypoventilation (e.g., caused by lung and airway disorders), low cardiac output (e.g., during shock states and myocardial infarction), and blood defects (e.g., sepsis, anemia and CO poisoning); inhalation or increased production of $CO_2$; and accumulation of organic or inorganic acids (e.g., lactic acid, hydrochloric acid and carbonic acid). Extreme acidosis occurs in the cells when physiological pH drops to approximately 7.0.

If, on the other hand, pH levels of the blood plasma and interstitial fluid are too high (i.e., greater than about 7.45), an excess of hydrogen ions will leave the cell, thereby increasing the alkalinity of the intracellular fluid and creating a condition called "alkalosis." Examples of conditions that cause physiological pH to rise may include hyperventilation, fever, some types of central nervous system damage, and loss of potassium ($K^+$), sodium ($Na^+$) and hydrochloric acid (HCl) due to pyloric obstruction, prolonged vomiting or diuretic alkalosis. Extreme alkalosis occurs in the cells when physiological pH increases to approximately 7.7.

As such, monitoring blood plasma pH may provide some indication of the severity of certain illnesses or medical conditions. Conventional electrodes used for monitoring intra-arterial or intravenous blood plasma pH generally include glass or antimony electrodes. A typical glass electrode consists of a glass bulb, which encloses a metal electrode immersed within an electrolytic solution. Unfortunately, conventional glass electrodes suffer from many disadvantages. For example, glass electrodes are often extremely fragile, and therefore, undesirably expensive to produce and transport. Due to their relatively high electrical impedance, glass electrodes also demonstrate a prolonged time response and require heavily shielded probe leads to reduce unwanted noise components in the probe signal. In addition, the inherent rigidity of glass electrodes does not allow for minimization of patient discomfort when measuring in vivo pH levels.

As yet another disadvantage, most glass electrodes require the use of an external reference electrode, which as described below, is undesirable for several reasons. Recently, combination pH and reference electrodes have been fabricated within a single glass enclosure. However, the present inventors are unaware of a commercially available combination pH and reference glass electrode having a size substantially less than 1.0 mm in diameter.

In an effort to overcome the disadvantages of glass electrodes, antimony electrodes have been constructed for use in monitoring in vitro and in vivo pH levels. As one advantage, antimony electrodes can be made much smaller and more robust than pH electrodes made from glass. In addition, the antimony electrode is a relatively low impedance device (e.g., 1 MΩ or less) compared to the glass electrode (e.g., 12 MΩ). As such, antimony electrodes demonstrate shorter time responses than glass electrodes and do not require shielding, in most cases.

However, conventional antimony electrodes suffer from their own disadvantages. In one example, a method of constructing an antimony electrode includes forming an antimony rod from which relatively small fragments are cut or otherwise detached from the rod. After attaching one of the fragments to a wire lead, the assembly is encased within a glass tube leaving an upper portion of the antimony fragment exposed for sensing purposes. Unfortunately, antimony electrodes formed in such a manner suffer from the effects of a rough sensing surface; namely, undesirable fluctuations in pH measurements.

In an effort to reduce signal fluctuations, another method has been disclosed in which an antimony fragment and attached wire lead are completely coated in a hard-setting acrylic resin. By grinding one end of the resin-coated electrode to produce a substantially flat planar surface, a portion of the antimony fragment is exposed for sensing purposes. Unfortunately, the grinding action tends to pull the exposed antimony portion away from the acrylic resin coating, resulting in the formation of micro-crevices between the exposed antimony portion and the acrylic resin coating. In some cases, fluids may become trapped within these micro-crevices, resulting in sample contamination and erroneous pH measurements when the electrode is transferred to another position. In addition, fluctuations in pH measurements may still occur if the exposed antimony portion does not exhibit a completely smooth sensing surface.

In addition to inconsistent and erratic pH measurements, the above-mentioned antimony electrodes suffer from several other disadvantages. As noted above, conventional antimony electrodes are typically encased within inflexible materials, such as glass tubes or hard-setting resins. These inflexible materials are not conducive to minimizing patient discomfort when measuring in vivo pH levels. In addition, the above-mentioned antimony electrodes require the use of external reference and temperature electrodes; the disadvantages of which will be described in more detail below.

pH-sensitive electrodes, such as the glass and antimony electrodes described above, are configured to provide an electrical potential that is sensitive to changes in hydrogen ion concentration. However, pH-sensitive electrodes must be combined with reference electrodes, which are configured to provide a constant electrical potential independent of hydrogen ion concentration, to determine the pH of a sample medium. In this manner, the pH may be determined by the "electrode potential difference," or the difference in electrical potentials measured by the pH-sensitive electrode (i.e., the active electrode) and the reference electrode.

As noted above, most conventional pH-sensitive electrodes are used in combination with external reference electrodes, which are coupled to the sample medium at a location spaced apart from the active electrode. Examples of conventional external reference electrodes include skin surface electrodes (e.g., a standard EKG electrode) and separate needle electrodes, which may be placed in the vicinity of the sample medium or simply within the patient's body (e.g., within any subcutaneous tissue). As another example, reference half-cells have also been combined with conventional pH-sensitive electrodes. In general, a reference half-cell is an external reference electrode, which is electrochemically coupled to the sample medium via a salt bridge, and typically includes a metal-chloride electrode (e.g., a calomel (Hg:HgCl) or Ag:AgCl electrode) immersed within an electrolyte. Unfortunately, due to the inevitable distance separating the active and reference electrodes, a decrease in accuracy and an increase in time response can be attributed to all external reference electrodes.

Due to the influence of temperature on antimony, pH measurements obtained with antimony electrodes are often offset, and thus, require temperature compensation to obtain "true" pH measurements. Previous attempts at temperature compensation include obtaining and manually entering a patient's body temperature into an analytical device. Alternatively, an external temperature electrode may be used to detect the temperature of an area somewhat removed from the antimony electrode. Unfortunately, such methods are often inconvenient and sometimes inaccurate (e.g., when the measured temperature differs from the temperature at the pH measurement site).

Therefore, a need exists for a pH-sensitive electrode that overcomes the disadvantages described above, and more specifically, for a combination pH probe having an antimony electrode, a reference electrode and a temperature electrode formed within a single probe housing. Such a combination pH probe would provide stable and accurate pH measurements, while demonstrating a time response, which is significantly faster than the time response of conventional electrodes. Preferably, the combination pH probe would provide a minimally invasive means for obtaining quick and accurate pH measurements within in vivo or in vitro samples of physiological fluids, such as blood plasma, gastric secretions, pancreatic secretions, saliva, and other bodily fluids.

In addition to physiological fluids, the combination probe would also provide a minimally invasive means for obtaining in vivo pH measurements of interstitial fluids within physiological tissues and muscles. As noted above, conventional electrodes are often used for monitoring changes in intra-arterial or intra-venous blood plasma pH. Due to the compensatory effects of buffering in the blood, however, such monitoring provides an undesirably late indication of underlying problems, which manifest originally within the affected tissues and muscles. Unfortunately, detecting a change in the blood plasma pH indicates that irreversible damage to the tissue cells has already occurred.

Recently, a few electrodes have been described as able to monitor pH levels within human or animal tissues, muscles and organs. Due to their relatively large size, however, these electrodes inevitably cause at least some amount of local tissue damage. In some cases, insertion of an electrode greater than 1.0 mm in diameter may inflict enough local tissue damage to cause intracellular release of substantial amounts of hydrogen ions, resulting in local ischemia and underestimated pH measurements.

Clearly, a need remains for a combination pH probe having pH-, reference-, and temperature-sensing capabilities formed within a probe housing, which is small enough for obtaining in vivo pH measurements within tissues and muscles without inflicting significant local tissue damage.

SUMMARY OF THE INVENTION

The problems outlined above may, in large part, be addressed by a minimally invasive, micro-sized pH probe having a pH-sensitive electrode, a reference electrode and a temperature electrode arranged within a housing of the probe. As used herein, the term "micro-sized" relates to an outer diameter, which eliminates or otherwise minimizes the amount of tissue damage caused by insertion of the pH probe into physiological tissues or muscles. In one example, an outer diameter of the probe is between about 0.5 mm and about 1.25 mm. Though substantially larger diameters are possible, an outer diameter of approximately 0.8 mm or less is preferred. As such, the pH probe disclosed herein may be particularly useful for obtaining in vivo pH measurements in delicate circumstances (e.g., monitoring myocardial metabolism during cardiac surgery or monitoring pH levels within neonates), in addition to circumstances normally encountered within the field of pH sensing.

In one embodiment, a pH probe for determining a pH level of a sample medium is disclosed herein. The term "sample medium", as used herein, may include any acid-base solution or any substance containing an acid-base solution therein. In a particular example, a sample medium may include any physiological medium, such as extracellular fluid (i.e., interstitial fluid or blood plasma) found within or between connective tissues, muscles and organs. However, the pH probe is not necessarily limited to measuring pH within only physiological mediums and may also be used in other applications, such as biotechnology and environmental sciences. As such, the pH probe described herein may also be used for measuring pH of foods, beverages, chemicals, drugs, natural and public water supplies, soil or any other medium normally monitored for pH.

In some cases, the pH probe may include a probe housing consisting of an inner tube concentrically arranged within an outer tube. Preferably, the inner and outer tubes are formed of relatively flexible materials, so as to minimize patient discomfort when obtaining in vivo pH measurements. In some cases, a lumen of the inner tube may include a pH-sensitive electrode having a sensing portion, which protrudes from a first end of the inner tube for detecting a signal used to determine the pH level of the sample medium. In other words, a sensing portion of the pH-sensitive electrode may be configured to detect an electrical potential (typically in milli-volts), which is responsive to changes in hydrogen ion concentration of the sample medium.

In a preferred aspect of the present invention, the sensing portion of the pH-sensitive electrode includes a smooth hemispherical tip, which is virtually free of micro-crevices or other blemishes that may otherwise cause undesirable fluctuations in pH measurements. In particular, the pH-sensitive electrode may be an antimony electrode having a sensing portion and a conductive portion. A method of forming the pH-sensitive electrode is also disclosed herein and may include forming the sensing portion by dipping one end of an antimony rod, or piece thereof, into a molten solution of antimony and/or antimony oxide. By allowing the sensing portion to harden while pointing in a downward direction, a completely smooth hemispherical tip is formed due, in part, to surface tension of the molten antimony.

In some cases, a reference electrode and a temperature electrode may be included within a space between the inner tube and the outer tube of the pH probe. The reference electrode may fill at least a portion of the space, while the temperature electrode may be arranged along one side of the space. Alternate arrangements of the reference and temperature electrodes within the pH probe are entirely possible and within the scope of the invention.

Regardless of arrangement, the reference electrode may be configured to provide a constant electrical potential (typically in milli-volts), which is independent of hydrogen ion concentration. In this manner, the pH level of the sample medium may be determined by the "electrode potential difference," or the difference in electrical potentials measured by the pH-sensitive electrode and the reference electrode. Electrode drift and other noise factors are advantageously reduced to a minimum by positioning the reference electrode within the pH probe housing, and thus, minimizing the distance between the pH-sensitive electrode and the reference electrode.

Regardless of arrangement, the temperature electrode may include a temperature sensitive element responsive over a substantially large range of temperature values (e.g., between about 0° C. and about 100° C.). By positioning the temperature electrode within the pH probe housing, the temperature sensitive element is able to detect a local temperature of the sample medium with an accuracy greater than previously possible with external temperature electrodes. In this manner, the pH probe of the present invention advantageously provides a more accurate means for correcting a temperature dependency of the electrical potential measured by the pH-sensitive electrode.

In a preferred aspect of the present invention, the pH probe includes one or more diffusion windows located within a sidewall of the outer tube. In some cases, the one or more diffusion windows may also be located proximate to a first end of the outer tube (e.g., within a part of the outer tube that is near the sensing portion of the pH-sensitive electrode). In general, the diffusion windows are configured to provide electrical coupling between the reference electrode and the sample medium. In particular, the diffusion windows allow a controlled amount of electrolytic solution to diffuse into the sample medium, thereby providing an electrochemical connection between the sample medium and the reference electrode.

In another embodiment, a system for monitoring a pH level of a sample medium is disclosed herein as including a pH probe having a pH-sensitive electrode, a reference electrode and a temperature electrode arranged within a flexible probe housing, as described above. In this manner, the pH-sensitive electrode may detect a voltage associated with the pH level of the sample medium, the reference electrode may detect a base voltage of the sample medium, and the temperature electrode may detect a temperature value of the sample medium. In addition, the system may include a processing means, which is coupled to the pH probe and configured to determine the pH level of the sample medium using the voltage, the base voltage and the temperature value.

In yet another embodiment, a method for manufacturing a pH probe is disclosed herein. In general, the method may include providing a probe housing having an inner tube concentrically arranged within an outer tube of the probe housing. In addition, the method may include forming one or more diffusion windows within a sidewall of the outer tube proximate to a first end of the outer tube. Furthermore, the method may include arranging a plurality of electrodes each having a sensing portion and a conductive portion within the probe housing. Such an arrangement may ensure that a sensing portion of one of the plurality of electrodes protrudes from a first end of the probe housing, while a conductive portion of each of the plurality of electrodes protrudes from a second end of the probe housing. Subsequently, the method may include sealing the first and second ends of the probe housing with a sealant material, such that only the protruding portions of the plurality of electrodes remain exposed.

In a preferred aspect of the present invention, the method may include inserting an electrolytic solution into a space bounded by the outer tube, the inner tube and the sealant material, such that an entirety of the space is filled with the electrolytic solution. A particular advantage of the current method may be realized by inserting the electrolytic solution during manufacturing of the probe, as opposed to conventional methods that require the solution to be inserted by an end-user immediately before using the probe. As such, the current method improves upon conventional methods by significantly reducing the probe preparation time (i.e., the amount of time needed to prepare the probe for use), as well as reducing the possibility for contamination (e.g., due to user-mediated loading of the electrolytic solution). The current method may also include sealing the one or more diffusion windows, such that evaporation and/or crystallization of the electrolytic solution are substantially prevented. In particular, the method may include placing a protective cap around the first end of the probe housing.

In yet another embodiment, a method for using a pH probe is disclosed herein. Such a method may include removing a protective cap, which extends around an outer tube of the probe housing to provide a hermetic and hydrophobic seal over the one or more diffusion windows. Subsequently, the method may include inserting the pH probe into a sample medium without first having to fill the space between the outer tube and the inner tube with an electrolytic solution. As noted above, the current method greatly reduces the probe preparation time and the possibility of contaminating the pH probe.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Figure 1:
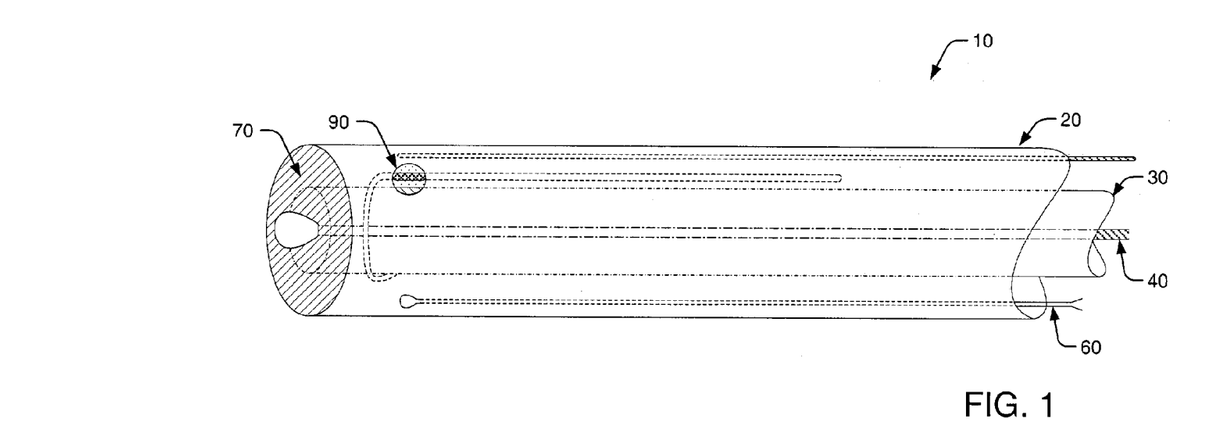
FIG. 1 is a three-dimensional view showing a top portion of an exemplary probe used for determining a pH level of a sample medium.
Figure 2:
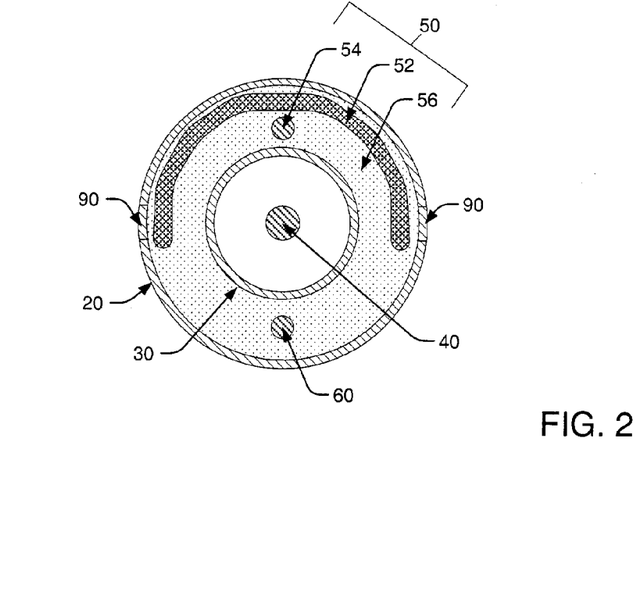
FIG. 2 is a lateral cross-sectional view of the pH probe of FIG. 1.
Figure 3:
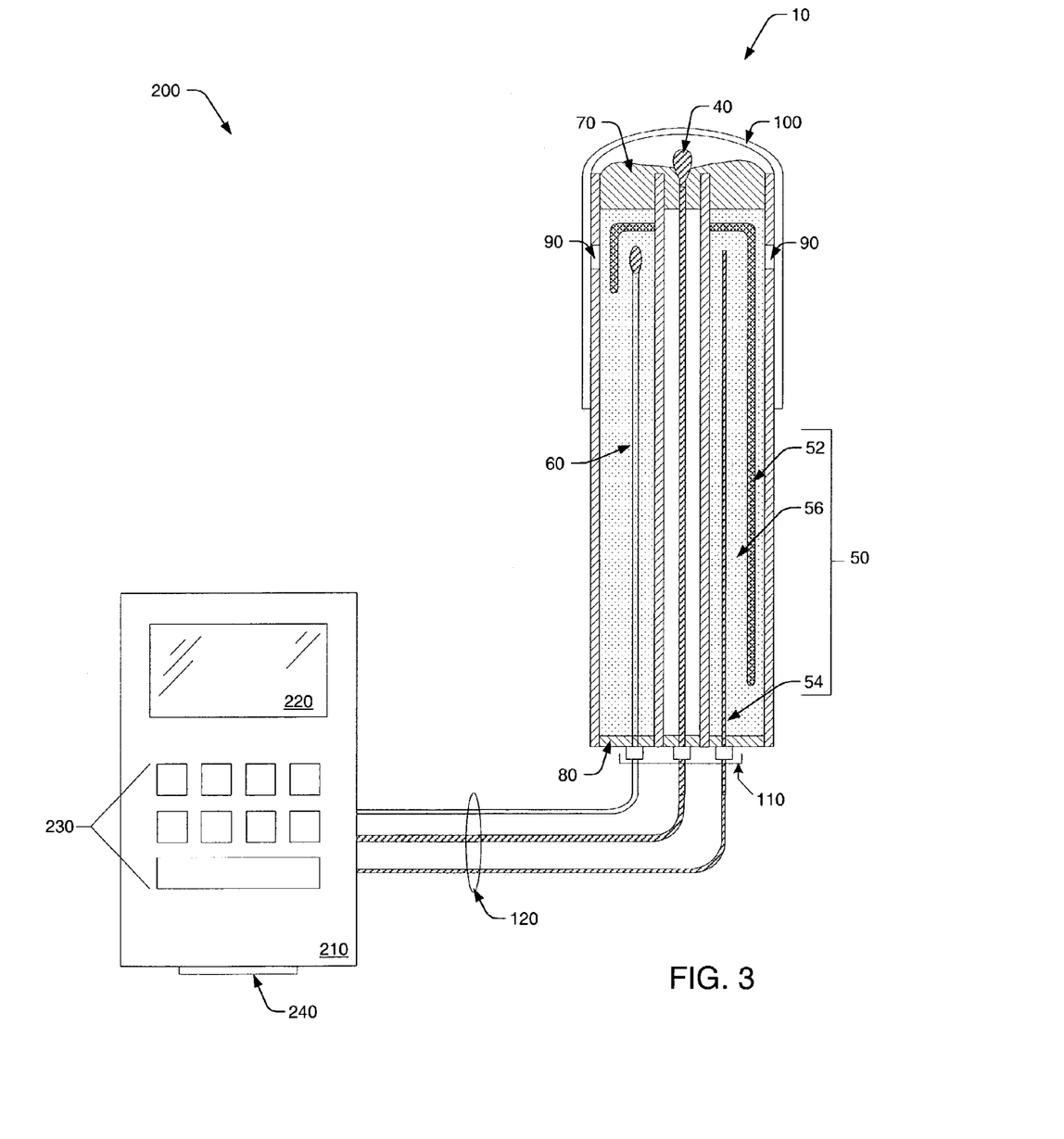
FIG. 3 illustrates an exemplary pH monitoring system including a longitudinal cross-sectional view of the pH probe of FIG. 1.

Turning to the drawings, exemplary embodiments of a pH probe in accordance with the present invention are shown in FIGS. 1–3. In particular, FIG. 1 illustrates a top portion of pH probe 10, while a lower portion of the probe is shown cut away for distinguishing probe elements. In addition, FIGS. 2 and 3 respectively illustrate lateral and longitudinal cross-sectional views of pH probe 10. Therefore, exemplary probe elements and their arrangements within pH probe 10 may be described concurrently in reference to FIGS. 1–3.

As shown in FIGS. 1–3, a probe housing of pH probe 10 includes outer tube 20 and inner tube 30. In most cases, inner tube 30 is concentrically arranged within outer tube 20, however, alternative arrangements are possible and within the scope of the invention. For example, inner tube 30 and outer tube 20 may be alternatively arranged in a side-by-side, or parallel, configuration. However, such a configuration is generally not preferred since it does not allow a uniform dispersion of electrolytic solution around the tube housing the pH-sensitive electrode. Regardless of arrangement, inner tube 30 and outer tube 20 are preferably formed from sections of substantially flexible tubing; examples of which may include polyamide tubing, polyethylene tubing, Teflon™ tubing, or any other flexible tubing approved for medical use (or at least highly resistant to chemicals and moisture). Such flexibility may advantageously minimize patient discomfort when pH probe 10 is used for obtaining in vivo pH measurements. When pH is to be measured within in vitro or non-medical samples, however, inner tube 30 and outer tube 20 may alternatively include other materials not approved for medical use (e.g., flexible PVC tubing).

A pH probe in accordance with the present invention is preferably "micro-sized," and, therefore, may be particularly suitable for use in delicate mediums (e.g., cardiac muscle, neonates, small animals, etc.). More specifically, pH probe 10 preferably demonstrates a relatively small outer diameter, which allows the probe to be utilized in such a manner. Though a minimum outer diameter of pH probe 10 is generally preferred, a range of outer diameters between about 0.5 mm and about 1.25 mm may be used to describe a "micro-sized" pH probe.

In addition, the probe housing of pH probe 10 is preferably configured to include a plurality of electrodes, and more specifically, to include pH-sensitive electrode 40, reference electrode 50 (shown in FIGS. 2 and 3) and temperature electrode 60. In most cases, pH-sensitive electrode 40 is arranged within a lumen of inner tube 30, while reference electrode 50 and temperature electrode 60 reside within a space between inner tube 30 and outer tube 20. Of course, alternate arrangements of the electrodes are possible, especially in cases where the configuration of the probe housing differs from that illustrated in FIGS. 1–3.

Figure 4:
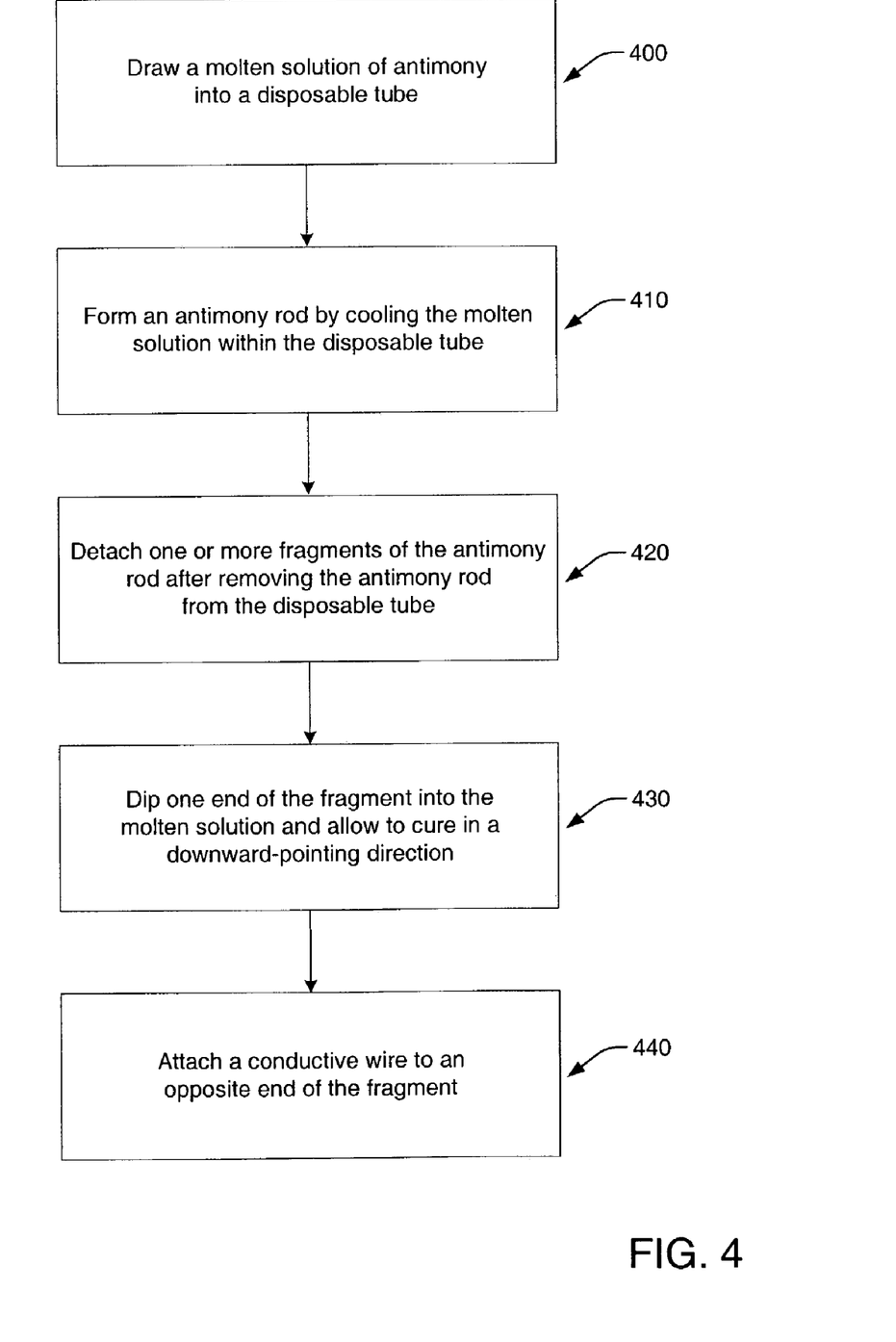
FIG. 4 is a flow-chart diagram illustrating an exemplary method of forming a pH-sensitive electrode included within the pH probe of FIGS. 1–3.

In general, pH-sensitive electrode 40 may be formed from any material sensitive to fluctuations in ion levels within a sample medium. Preferably, pH-sensitive electrode 40 is formed from antimony (Sb); though other materials known for having pH sensing capabilities (e.g., palladium) may alternatively be used. An exemplary method of forming an antimony pH-sensitive electrode is illustrated in FIG. 4 and described in more detail below.

In general, reference electrode 50 may include one or more electrolytically coupled elements; the combination of which fills at least a portion of the space between inner tube 30 and outer tube 20. In a preferred embodiment, reference electrode 50 consists of a plurality of elements, e.g., porous thread material 52, electrical conductor 54 and electrolytic solution 56, which are arranged within the space between the inner and outer tubes. In some cases, porous thread material 52 is arranged along one side of the space and extends in a continuous manner to an opposite side of the space, as shown in FIGS. 1 and 3. Alternatively, porous thread material 52 may be arranged along only the one side, only the opposite side, or may continuously or periodically alternate between sides (e.g., by spiraling around a perimeter of inner tube 30). Regardless of arrangement, porous thread material 52 may be formed of any fibrous material capable of absorbing electrolytic solution 56. For example, porous thread material 52 is preferably formed as a cotton wick; however, any other flexible material having absorption capabilities (e.g., uncoated dental floss) can alternatively be used.

In some cases, electrical conductor 54 is arranged along the one side of the space, as shown in FIGS. 1 and 3. In other cases, however, electrical conductor 54 may be arranged along the opposite side of the space or may alternate between sides, similar to the arrangement of porous thread material 52 described above. Electrical conductor 54 may include any metallic conductor; however, the stability of reference electrode 50 should be considered when selecting a material composition for electrical conductor 54.

More specifically, chemical activity within reference electrode 50 may introduce noise within the pH signal by inducing voltage fluctuations in the absence of electrode input. Fortunately, such noise may be reduced or substantially eliminated with proper choice of materials and/or by special treatment of the materials used to form electrical conductor 54. To improve the stability of reference electrode 50, electrical conductor 54 preferably contains at least some amount of silver and at least some amount of chloride. For example, electrical conductor 54 may be formed by coating substantially any metallic wire with silver chloride.

In a preferred embodiment, however, electrical conductor 54 is formed by coating a silver wire with silver chloride to maximize the stability of reference electrode 50. In some cases, coating may be performed electrolytically by placing two pieces of silver wire into a salt solution (e.g., a bromide-free sodium-chloride solution). By connecting the two pieces to opposite terminals of a voltage source, silver ions from one piece of silver wire diffuse into the solution to combine with chloride ions. Neutral silver chloride molecules produced by the combination may then electrolytically coat the other piece of silver wire. In other cases, however, coating may be achieved by dipping a silver wire into a molten solution of silver chloride.

In some cases, electrolytic solution 56 fills at least a portion of the space to provide an electrical connection between porous thread material 52 and electrical conductor 54. More specifically, electrolytic solution 56 may fill the space bound by inner tube 30, outer tube 20 and sealant materials 70 and 80, which as discussed in more detail below, provide a hydrophobic seal at the distal ends of pH probe 10. In general, electrolytic solution 56 may be any nonmetallic conductor in which electrical current is carried by the movement of ions. Thus, electrolytic solution 56 may also be referred to as an "electrolyte." Preferably, electrolytic solution 56 is a viscous fluid, or gel, consisting of one or more chlorides selected from a group comprising potassium chloride (KCl), silver chloride (AgCl) and sodium chloride (NaCl). However, electrolytic solution 56 is not limited to only those chlorides discussed herein, and may alternatively include other chlorides capable of performing the same function.

In general, temperature electrode 60 may include any appropriately sized device capable of detecting temperatures within an aqueous solution. As used herein, the term "appropriately sized" refers to an outer diameter of temperature electrode 60, which allows electrode 60 to be incorporated into pH probe 10. As such, the size of temperature electrode 60 may be directly dependent on the size of pH probe 10, and vice versa. In most cases, a temperature electrode configured for use within the micro-sized pH probe of the present invention will have an outer diameter substantially less than or equal to about 0.5 mm. Preferably, the outer diameter of temperature electrode 60 is less than or equal to about 0.33 mm. In some cases, temperature electrode 60 may be responsive within a range of temperatures that occur within a particular sample medium. It may be preferred, however, that temperature electrode 60 be responsive to a substantially large range of temperature values (e.g., about 0° C. to about 100° C.) to avoid limiting the pH probe to operation within only particular mediums.

Exemplary devices that may qualify as candidates for temperature electrode 60 include thermistors, thermocouples and resistance temperature detectors (RTDs). However, thermistors may be generally preferred due to the increased circuit complexity associated with thermocouples (i.e., thermocouples typically require a reference junction) and the relatively higher cost of RTDs. In general, temperature electrode 60 may include any temperature sensitive device, which demonstrates an acceptable trade-off between minimum size and cost, and maximum accuracy.

Furthermore, each of the electrodes within pH probe 10 may be described as including a "sensing portion" and a "conductive portion." As shown in FIGS. 1 and 3, for example, a sensing portion of pH-sensitive electrode 40 is the portion protruding from a first end of inner tube 30, while sensing portions of reference electrode 50 and temperature electrode 60 remain within the space between inner tube 30 and outer tube 20. On the other hand, conductive portions of each of the electrodes may be indicated by the portions, which extend outward from within corresponding opposite (i.e., second) ends of inner tube 30 and outer tube 20. In this manner, "sensing portions" may be configured for detecting signals, whereas "conductive portions" may be configured, at least in part, for transmitting the detected signals to output terminal 110 of pH probe 10.

As noted above, a means is provided for sealing the distal ends (i.e., the first and second ends) of pH probe 10. For example, sealant material 70 may be applied (or arranged proximate) to the first ends of inner tube 30 and outer tube 20, such that only the sensing portion of pH electrode 40 protrudes from a surface of sealant material 70. As such, sealant material 70 may include any means by which to provide a hydrophobic seal between the protruding sensing portion and the first ends of the inner and outer tubes. In addition, sealant material 80 may be applied (or arranged proximate) to the second ends of inner tube 30 and outer tube 20, such that only the conductive portions of each of the electrodes protrude from a surface of sealant material 80. As such, sealant material 80 may include any means by which to provide a hydrophobic seal between the protruding conductive portions and the second ends of the inner and outer tubes. In this manner, sealant materials 70 and 80 serve to electrically isolate pH-sensitive electrode 40 from electrodes 50 and 60, in addition to preventing excess leakage of electrolytic solution 56 into the sample medium. Preferably, sealant materials 70 and 80 are comprised of any acrylic, epoxy or ion exchange resins, which are hydrophobic, robust and substantially non-toxic to humans or animals.

In a preferred aspect of the present invention, pH probe 10 includes one or more diffusion windows 90 located within a sidewall of outer tube 20. In general, diffusion windows 90 are located proximate to the first end of outer tube 20 and are configured to provide electrical coupling between reference electrode 50 and the sample medium. Diffusion windows 90 also provide a means for temperature electrode 60 to detect a local temperature of the sample medium. In most cases, diffusion windows 90 include approximately one to four small "windows" or openings by which electrolytic solution 56 may pass unimpeded through the sidewall of outer tube 20. In this manner, diffusion windows 90 beneficially allow a controlled amount of electrolytic solution 56 to quickly diffuse into the sample medium, thereby providing an electrolytic connection between the sample medium and portions of porous thread material 52 arranged in the vicinity of diffusion windows 90.

Alternatively, diffusion windows 90 may be sealed with a porous plug, such as those conventionally made of cotton or wood. Unfortunately, a porous plug may impede diffusion of electrolytic solution 56, thereby increasing a time response of the pH probe. As such, diffusion windows 90 preferably include a number of unsealed openings having a size and arrangement appropriately chosen to ensure quick diffusion of a controlled amount of electrolytic solution 56 into the sample medium. As described herein, a "controlled amount" may be any amount, which provides an electrolytic connection between the reference electrode and the sample medium without contaminating the sample medium with excessive solution. In one example, pH probe 10 may include two diffusion windows having a substantially circular configuration and spaced approximately 180° apart. However, the number, shape, size and spatial arrangement of diffusion windows 90 may be individually chosen to provide an appropriate amount of electrolytic solution for a given application.

In order to prevent evaporation or crystallization of electrolytic solution 56, diffusion windows 90 may be sealed with protective cap 100 during storage and prior to use of pH probe 10. In general, protective cap 100 is formed of a pliable plastic material, which extends around the first end of outer tube 20 to provide a hydrophobic and hermetic seal over diffusion windows 90. In some cases, protective cap 100 may be formed as a tubular sheath encompassing only the perimeter of the outer tube, as shown in FIG. 5C. In other cases, however, protective cap 100 may enclose the exposed sensing portion of the pH-sensitive electrode in addition to the perimeter of the outer tube, as shown in FIG. 3.

An exemplary system for monitoring a pH level of a sample medium will now be described in further reference to FIG. 3. System 200 preferably includes pH probe 10 having pH electrode 40, reference electrode 50 and temperature electrode 60 arranged within a flexible probe housing, as described above. In this manner, pH electrode 40 may be configured to detect a voltage associated with the pH level of the sample medium, reference electrode 50 may be configured to detect a base voltage of the sample medium, and temperature electrode 60 may be configured to detect a temperature value of the sample medium.

Also included within system 200, processing means 210 is coupled to receive the voltage, the base voltage and the temperature value from pH probe 10. In some cases, processing means 210 and pH probe 10 are coupled via probe leads 120 and probe output terminal 110, as shown in FIG. 3. However, such coupling is not necessarily limited to the embodiment shown in FIG. 3, and may alternatively include any other means by which to provide a "wired" or "wireless" connection between processing means 210 and pH probe 10. In addition, processing means 210 may be configured, in some cases, to determine the pH level of the sample medium using the voltage, the base voltage and the temperature value.

In some cases, processing means 210 may be a standard electrical potential measuring device (e.g., a voltmeter) or one calibrated to read directly in pH (e.g., a pH meter). In a preferred embodiment, however, processing means 210 includes a processor (not shown), display screen 220 and one or more user-actuated controls 230. As such, processing means 210 may be a hand-held or bench-top device containing electronic hardware and/or software appropriately chosen to provide a suitable interface between the probe data (i.e., the voltage, the base voltage and the temperature value) and the display screen. In this manner, the probe data and/or the pH level may be displayed on display screen 220. As an alternative or addition to display screen 220, processing means 210 may include output port 240 for transmitting an analog or digital signal, which may represent the probe data and/or the pH level, to an external processing device (e.g., a computer) or an external display device (e.g., a computer monitor). In this manner, the external processing device may alternatively be used to determine the pH level of the sample medium.

In addition, processing means 210 may be configured for calibrating the pH-sensitive electrode. Exemplary calibration procedures are described in more detail below. In general, calibration is often necessary due to slight differences in the construction of individual electrodes and other factors that may influence electrode measurements. For example, processing means 210 may also be configured to correct a temperature- and/or oxygen-dependent offset in the pH measurement, and thus, may be configured to provide a more convenient and accurate determination of pH.

Conventional methods have used monocrystalline antimony to form antimony electrodes. However, such methods tend to produce expensive and labor-intensive electrodes, which if not perfectly formed, suffer from accuracy, stability and reproducibility problems. Though pH-sensitive electrode 40 may be formed of monocrystalline antimony, in some cases, electrode 40 is preferably formed from ultra-pure antimony (i.e., 99.9999% antimony), which is significantly less expensive and labor intensive than its monocrystalline counterpart. Alternative forms of antimony not specifically discussed herein may also be used to construct pH-sensitive electrode 40.

As shown in FIG. 4, the preferred method of forming pH sensitive electrode 40 may begin by heating the ultra-pure antimony to a temperature high enough to transform the antimony into a molten solution (e.g., the melting temperature of antimony is about 630° C.). The method continues by drawing the molten solution of antimony into a disposable tube, such as a thin glass capillary tube (step 400). An inner diameter of the glass capillary tube may be less than or equal to the inner diameter of inner tube 30 (e.g., about 0.4 mm to about 1.0 mm). In general, the molten solution contains at least some amount of antimony. More specifically, the molten solution may contain pure antimony, but may alternatively comprise a mixture of antimony and antimony oxide. As a result of the melting process, for example, a portion of the pure antimony may be oxidized to form the mixture of antimony and antimony oxide.

Next, the molten solution may be cooled slowly within the disposable tube to form a solid antimony rod (step 410). Such slow cooling promotes large crystal growth, which in turn, enhances the stability of the pH-sensitive electrode. After cooling, one or more fragments may be cut, broken or otherwise detached from the antimony rod after the rod is removed from the disposable tube (step 420). In general, a diameter of a single fragment may be less than or equal the inner diameter of inner tube 30, and one or more fragments may be used to make individual pH-sensitive electrodes. Preferably, a single fragment is used to construct an electrode of minimum size.

Next, one end of an antimony fragment may be dipped into molten antimony, or more specifically, into a molten solution of antimony and antimony oxide to form a sensing portion of the pH-sensitive electrode (step 430). By allowing the sensing portion to harden while pointing in a downward direction, a completely smooth hemispherical tip is formed due, in part, to surface tension of the molten antimony. In this manner, the sensor tip (or sensing portion) of the pH-sensitive electrode may comprise a very thin layer of antimony having an oxidized outer surface. To complete construction of the pH-sensitive electrode, a conductive wire is attached to an opposite end of the antimony fragment (step 440). Though the conductive wire is preferably solder attached to the antimony fragment, other means of attachment may alternatively be used. As such, the antimony fragment and conductive wire may form the conductive portion of the pH-sensitive electrode.

In this manner, the present method overcomes the disadvantages of previous methods of forming an antimony electrode. For example, the present method provides an antimony electrode having a completely smooth sensing surface, and thus, eliminates or substantially reduces the pH measurement fluctuations caused by micro-crevices or other blemishes in the surface. As such, a pH-sensitive electrode formed in accordance with the present method demonstrates a significantly greater stability than conventional pH-sensitive electrodes. In addition, the present method demonstrates a reduction in cost and complexity over conventional electrodes.

Figure 5A:
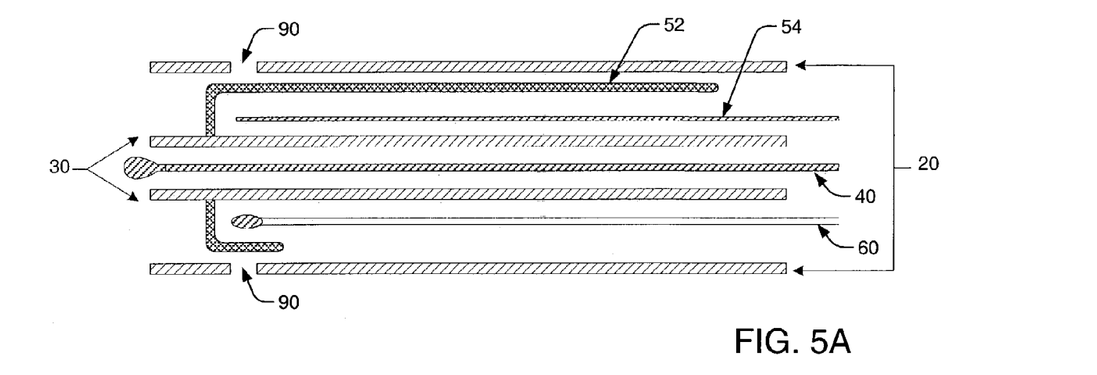
FIGS. 5A–C illustrate an exemplary method for manufacturing the pH probe of FIGS. 1–3.
Figure 5B:
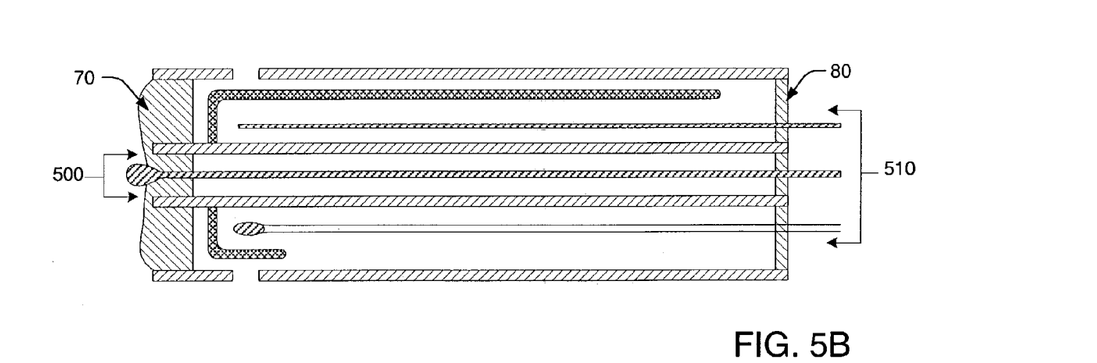
Figure 5C:
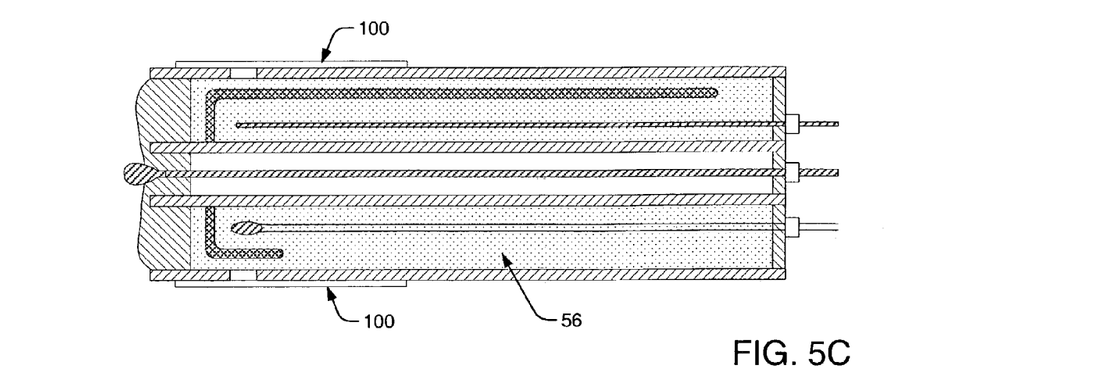

FIGS. 5A–C illustrate a preferred method of manufacturing pH probe 10. As shown in FIG. 5A, the method may begin by providing a probe housing, which as described above, preferably includes an inner tube (30) concentrically arranged within an outer tube (20). Next, one or more diffusion windows (90) may be formed within a sidewall of the outer tube. In some cases, the diffusion windows are formed by means of puncturing (e.g., with a micro-sized drill bit), melting (e.g., with a laser beam) or drilling (e.g., with a micro-sized drill bit) through the sidewall of the outer tube. In most cases, however, the diffusion windows are formed prior to arranging the inner tube within the outer tube to avoid damaging the inner tube. In any case, approximately one to four diffusion windows are usually formed proximate to a first end of the outer tube (i.e., within a part of the outer tube that is near the sensing portion of pH-sensitive electrode 40).

Subsequently, a plurality of electrodes (40, 50, 60), each having a sensing portion and a conductive portion, may be arranged within the probe housing. In general, one of the plurality of electrodes (40) may be arranged within the inner tube, while the remaining electrodes (50, 60) are arranged within a space between the inner tube and the outer tube. In addition, the plurality of electrodes may be arranged such that a sensing portion of one of the plurality electrodes (40) protrudes from a first end of the probe housing, while a conductive portion of each of the plurality of electrodes (40, 50, 60) protrudes from a second end of the probe housing. More specifically, the pH-sensitive electrode (40) may be positioned within the probe housing so that only a sensing portion of the electrode is allowed direct contact with the sample medium. Indirect contact between the reference electrode (50), the temperature electrode (60) and the sample medium is provided via the diffusion windows (90) and the electrolytic solution (56).

Numerous advantages arise from arranging the plurality of electrodes within the probe housing. By positioning the pH-sensitive electrode within the inner tube, for example, the pH-sensitive electrode may be electrically isolated from the electrodes positioned within the outer tube. In addition, positioning the reference electrode within the probe housing minimizes the distance between the pH-sensitive electrode and the reference electrode. Such an arrangement advantageously reduces a time response of the probe, while minimizing electrode drift and other noise factors normally associated with external reference electrodes. Furthermore, positioning the temperature electrode within the probe housing allows the temperature electrode to detect a local temperature of the sample medium, as opposed to a general temperature detected by an external temperature electrode. Thus, the internal temperature electrode described herein may provide a greater accuracy than possible with external temperature electrodes. Consequently, the arrangement disclosed herein provides a pH probe, which responds faster and with greater accuracy and stability than previously possible.

Next, the method includes sealing the first and second ends of the probe housing with a sealant material (70, 80), as shown in FIG. 5B. In particular, the first and second ends of the probe housing are sealed, such that only the protruding portions (500, 510) of the plurality of electrodes remain exposed. More specifically, any space between the protruding portions and the ends of the probe housing is filled entirely with sealant material to avoid contamination of the sample medium and/or contamination within the probe. In this manner, the sealant material prevents excess leakage of the electrolytic solution (56) into the sample medium, and also prevents fluids from the sample medium from entering the probe (which, as described above, may cause erratic pH measurements). In addition, the sealant material may further electrically isolate the pH-sensitive electrode from the remaining electrodes within the probe housing.

In a subsequent step of the method, the electrolytic solution (56) may be inserted into a space bounded by the outer tube, the inner tube and the sealant material, as shown in FIG. 5C. More specifically, the entire space is filled with electrolytic solution to avoid air bubbles or incomplete filling, which may otherwise cause pH measurements to be erratic. In some cases, a vacuum may be created within the space before inserting the electrolytic solution to ensure complete filling of the space. The vacuum, as well as the insertion of electrolytic solution, is achieved via the one or more diffusion windows. Alternatively, the electrolytic solution may be forcefully inserted through the diffusion windows to completely fill the space. In such a case, it may be necessary to form a small hole within the outer tube to allow air within the space to escape; the small hole may be subsequently filled with a sealant material.

In a preferred aspect of the present invention, the electrolytic solution is inserted during a manufacturing step of the probe, as opposed to packaging the probe dry and relying on a user to insert the solution. By doing so, the present method significantly reduces the probe preparation time (i.e., the time needed to prepare the probe for use), and eliminates the possibility of contamination due to user-mediated loading of the probe. Since the pH probe may be stored for a period of time, the diffusion windows are sealed with a protective cap (100) to prevent evaporation or crystallization of the electrolytic solution.

Figure 6:
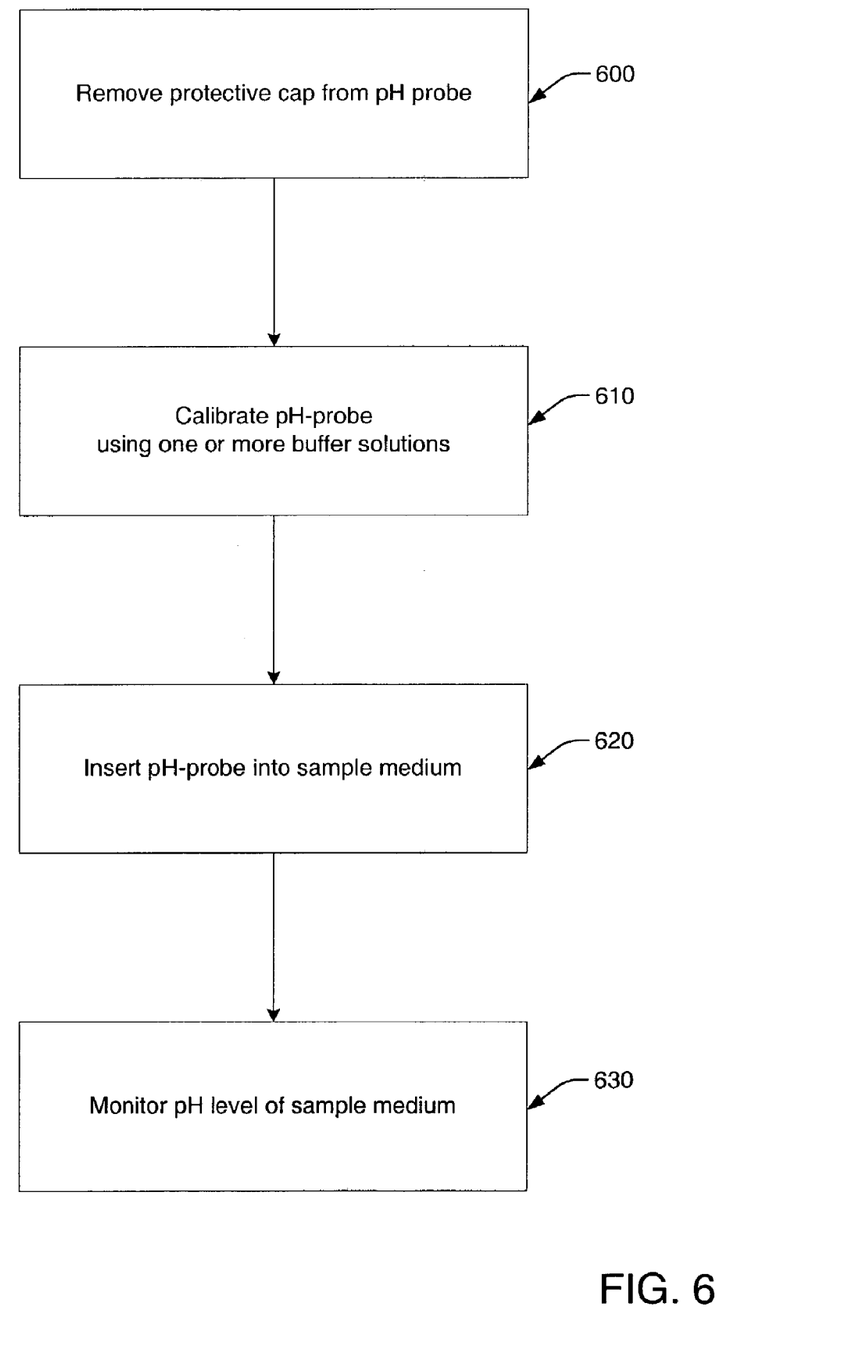
FIG. 6 is a flow-chart diagram illustrating an exemplary method for using the pH probe of FIGS. 1–3.

FIG. 6 illustrates a preferred method of using pH probe 10. In some cases, the method may begin by removing the protective cap overlying the one or more diffusion windows (step 600). After removing the protective cap, the pH probe may be calibrated using one or more standard buffer solutions (step 610). In some cases, the pH probe may be calibrated by placing the exposed sensing portion of the pH-sensitive electrode into at least one buffer solution having a pH level similar to an expected pH level of the sample medium. Though previous investigators have reported a non-linear response for antimony electrodes over the entire pH scale, others indicate that the response may be substantially linear within at least the calibration range (e.g., about 6.8 to about 7.5 if using 6.84 and 7.45 calibrated buffer solutions). Therefore, it may be beneficial to calibrate the pH probe using a buffer solution having a pH level similar to an expected pH level, especially when obtaining pH measurements within physiological mediums.

In addition, antimony electrodes are often affected by temperature and oxygen tension within the sample medium. For example, false pH measurements may occur when a sample temperature differs from the temperature at which a pH probe is calibrated. In particular, higher sample temperatures may cause pH measurements to appear higher (i.e., over exaggerate the degree of alkalosis), while lower sample temperatures may cause pH measurements to appear lower (i.e., over exaggerate the degree of acidosis) than the actual pH of the sample medium. Therefore, it may be beneficial, in some cases, to calibrate the pH probe using a buffer solution having a temperature similar to a temperature of the sample medium. Alternatively, or in addition to, temperature compensation may be performed to eliminate any temperature-dependent offset in the pH measurement.

In the same manner, false pH measurements may occur if oxygen levels differ between the sample medium and the buffer solution used for calibration. Contrary to the effect of temperature, however, higher oxygen levels in the sample medium cause pH measurements to appear lower, while lower oxygen levels in the sample medium cause pH measurements to appear higher than the actual pH of the sample medium. Therefore, it may also be beneficial to calibrate the pH probe using a buffer solution having an oxygen level similar to that of the sample medium. In some cases, remaining oxygen-dependent offsets may be compensated for analytically.

In a preferred embodiment, the pH probe is generally calibrated using two or more calibrated buffer solutions and a neutral solution, such as distilled or de-ionized water. After connecting the pH probe to the probe meter (e.g., processing means 210 of FIG. 3) and removing the protective cap, the tip of the pH probe is immersed within the neutral solution until the pH probe becomes stable (e.g., 30 seconds, or until the pH probe reaches an equilibrium state). The pH probe may be removed from the neutral solution and quickly dried before immersing the tip of the pH probe into a calibrated buffer solution having a substantially acidic pH (e.g., a solution having a pH less than 7.0). In one example, the acidic calibrated buffer solution may have a pH of about 6.84. Once the pH probe is stable (e.g., after 15 seconds of immersion), a pH of the acidic solution is measured and the probe is removed. Once again, the pH probe may be dried, and the above steps may be repeated for a calibrated buffer solution having a substantially alkaline pH (e.g., a solution having a pH greater than 7.0). In one example, the alkaline calibrated buffer solution may have a pH of about 7.45. In some cases, the probe may be ready for use after drying the probe once more. Alternatively, the above steps may be repeated as necessary.

After calibration, the pH probe may be inserted into the sample medium (step 620) for monitoring the pH level of the sample medium (step 630). As noted above, the probe housing is constructed of flexible tubing, so as to minimize patient discomfort when obtaining in vivo pH measurements. Due to the flexibility of the housing, however, it may be necessary to insert the pH probe through a small needle introducer, or rigid tube used for puncturing an outer surface of the sample medium. In most cases, 18-, 19- or 20-gauge introducers (i.e., about 1.24 mm, 1.07 mm and 0.89 mm in diameter, respectively) may accommodate the micro-sized pH probe of the present invention. In some cases, however, introducers of different sizes may be appropriate, whereas, in other cases, an introducer may not be required to insert the pH probe.

In general, the micro-sized pH probed described herein may be used for monitoring or measuring pH within any acid-base solution or substance containing an acid base solution. For example, the pH probe may be used to measure pH in the fluids of calibrated buffer solutions or other media, such as meats, fruits, vegetables, and other food and beverage products. The pH probe may also be used to measure the pH of certain drugs and chemicals to ensure uniformity during processing. In a preferred embodiment, the pH probe is used for measuring the pH of physiological fluids. For example, the pH probe may be used in dentistry for measuring pH in dental plaque and oral secretions, or in medicine for measuring pH in blood plasma, gastric secretions and pancreatic secretions.

However, a pH probe in accordance with the present invention is particularly suitable for monitoring or measuring pH of extracellular fluids within human or animal tissues and muscles. In particular, the pH probe described herein is both micro-sized and minimally invasive, and therefore, may be used for obtaining in vivo pH measurements within tissues and muscles without inflicting significant local tissue damage (e.g., due to having a diameter substantially less than 1.0 mm). As such, the pH probe can be used to provide an earlier indication of acidosis or alkalosis by measuring pH within the affected tissues or muscles, as opposed to measuring the pH of blood plasma (which provides a relatively late indication). For example, the pH probe may provide an early indication of inadequate oxygen perfusion within the affected tissues or muscles. The pH probe may be especially suitable for use in delicate circumstances (e.g., monitoring cardiac muscle, neonates, small animals, etc.) due to the minimum amount of trauma inflicted by insertion of the pH probe within the sample medium or the patient.

In addition, the micro-sized pH probe may be useful for continual pH monitoring within human or animal tissue, muscle, organs or blood. For example, the micro-sized pH probed may be used for monitoring pH in neonates, critical care patients (e.g., patients in shock or experiencing a heart attack), patients with blood disorders, during surgical procedures and numerous other clinical applications. In particular, the pH probe may be used for directly monitoring a clinical situation of a patient undergoing cardiac surgery, which as described above, was previously infeasible due to conventional electrodes being substantially greater than 1.0 mm in diameter. In addition, the pH probe may be used for monitoring neonatal sepsis (i.e., a blood bacterial infection plaguing infants less than four weeks of age). Currently, neonatal sepsis is monitored by measuring the infant's body temperature, which is an indication of the presence of infection.

It will be appreciated to those skilled in the art having the benefit of this disclosure that this invention is believed to provide a minimally invasive, micro-sized pH probe having a pH-sensitive electrode, a reference electrode and a temperature electrode arranged therein. Further modifications and alternative embodiments of various aspects of the invention will be apparent to those skilled in the art in view of this description. It is intended that the following claims be interpreted to embrace all such modifications and changes and, accordingly, the specification and drawings are to be regarded in an illustrative rather than a restrictive sense.

What is claimed is:

1. A probe for determining a pH level of a sample medium, the probe comprising:
   a flexible outer tube having a flexible inner tube concentrically arranged therein, wherein a lumen of the inner tube comprises a pH-sensitive electrode having a conducting portion and a sensing portion, which protrudes from a first end of the inner tube for detecting a signal used to determine the pH level of the sample medium, wherein:
   the conducting portion comprises one or more antimony rods; and
   the sensing portion comprises a smooth hemispherical tip formed by dipping one end of the antimony rods into liquefied antimony and allowing the sensing portion to harden while pointing in a downward direction;
   wherein a space between the inner tube and the outer tube comprises:

a reference electrode configured to fill at least a portion of the space;

a temperature electrode arranged along one side of the space; and wherein a sidewall of the outer tube comprises one or more diffusion windows located proximate to a first end of the outer tube to provide electrical coupling between the reference electrode and the sample medium.

2. The probe as recited in claim 1, further comprising a sealant applied to the first ends of the inner and outer tubes, wherein the sealant provides a hydrophobic seal extending between the sensing portion of the pH-sensitive electrode and the first ends of the inner and outer tubes.

3. The probe as recited in claim 1, wherein the temperature electrode comprises a temperature sensitive element configured to detect temperature values between about 0° C. and about 100° C., and wherein an outer diameter of the temperature sensitive element is substantially less than 0.5 mm.

4. The probe as recited in claim 1, wherein the reference electrode comprises:

a porous thread material arranged along the one side and extending in a continuous manner to an opposite side of the space;

an electrical conductor arranged along the one side or the opposite side of the space; and an electrolytic solution filling at least a portion of the space and configured to provide an electrical connection between the porous thread material and the electrical conductor.

5. The probe as recited in claim 4, wherein portions of the porous thread material are arranged in the vicinity of the one or more diffusion windows.

6. The probe as recited in claim 4, wherein the porous thread material comprises a cotton wick.

7. The probe as recited in claim 4, wherein the electrical conductor comprises a metal wire containing at least some amount of silver and at least some amount of chloride.

8. The probe as recited in claim 4, wherein the electrolytic solution comprises a viscous fluid consisting of one or more chlorides selected from a group comprising potassium chloride, silver chloride and sodium chloride.

9. The probe as recited in claim 4, wherein the pH-sensitive electrode, the reference electrode and the temperature electrode each comprise a conductive portion, which extends outward from within corresponding second ends of the inner and outer tubes in a direction opposite to the first ends of the inner and outer tubes.

10. The probe as recited in claim 9, further comprising a sealant applied to the second ends of the inner and outer tubes, wherein the sealant provides a hydrophobic seal, which fills a space between the pH-sensitive electrode, the reference electrode, the temperature electrode and the second ends of the inner and outer tubes, such that only the conductive portions protrude from a surface of the sealant.

11. The probe as recited in claim 1, wherein an outer diameter of the probe is between about 0.5 mm and about 1.25 mm.

12. A system for monitoring a pH level of a sample medium, the system comprising:

a pH probe comprising:

a flexible probe housing comprising an inner tube concentrically arranged within an outer tube, which has one or more diffusion windows formed therein;

a pH-sensitive electrode arranged within the inner tube and partially protruding from a first end of the inner tube, wherein the pH-sensitive electrode comprises an antimony rod having a smooth hemispherical tip, which is configured to detect a voltage associated with the pH level of the sample medium;

a reference electrode arranged within a space between the inner tube and the outer tube, wherein the reference electrode is configured to detect a base voltage of the sample medium;

a temperature electrode arranged along one side of the space, wherein the temperature electrode is configured to detect a temperature value of the sample medium; and a processing means coupled to the pH probe and configured to determine the pH level of the sample medium using the voltage, the base voltage, and the temperature value.

13. The system as recited in claim 12, wherein the processing means comprises an electrical potential measuring device.

14. The system as recited in claim 13, wherein the processing means comprises a processor, a display screen, and one or more user-actuated controls.

15. The system as recited in claim 14, wherein the processing means further comprises an output port for transmitting an analog signal to a display device.

16. The system as recited in claim 14, wherein the pH level and the temperature value are displayed upon the display screen.

17. The system as recited in claim 12, wherein the pH probe comprises an outer diameter of about 1.25 mm or less.

* * * * *